(12) United States Patent
King et al.

(10) Patent No.: US 9,360,410 B2
(45) Date of Patent: *Jun. 7, 2016

(54) METHOD AND PARTICLE ANALYZER FOR DETERMINING A BROAD PARTICLE SIZE DISTRIBUTION

(71) Applicant: ProteinSimple, Santa Clara, CA (US)

(72) Inventors: Frederick David King, Richmond (CA); Clark Adrien Merchant, Kanata (CA); Peter Oma, Ottawa (CA)

(73) Assignee: ProteinSimple, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/222,776

(22) Filed: Mar. 24, 2014

(65) Prior Publication Data

US 2015/0070699 A1 Mar. 12, 2015

Related U.S. Application Data

(63) Continuation of application No. 13/097,285, filed on Apr. 29, 2011, now Pat. No. 8,681,215.

(51) Int. Cl.
| | |
|---|---|
| *G01N 15/02* | (2006.01) |
| *G01N 15/14* | (2006.01) |
| *G01N 21/51* | (2006.01) |
| *G01N 21/53* | (2006.01) |
| *G01N 21/64* | (2006.01) |

(52) U.S. Cl.
CPC ........ *G01N 15/0227* (2013.01); *G01N 15/0211* (2013.01); *G01N 15/1463* (2013.01); *G01N 21/51* (2013.01); *G01N 21/53* (2013.01); *G01N 21/64* (2013.01); *G01N 2015/1486* (2013.01); *G01N 2015/1493* (2013.01)

(58) Field of Classification Search
CPC ............... G01N 15/1463; G01N 2015/1486; G01N 2015/1493; G01N 15/0211; G01N 15/0227; G01N 21/51; G01N 21/53; G01N 21/64
USPC ........... 348/135; 356/335, 336, 436, 440, 441
See application file for complete search history.

(56) References Cited

U.S. PATENT DOCUMENTS

| | | | | |
|---|---|---|---|---|
| 5,822,055 | A * | 10/1998 | Tsai et al. | 356/237.1 |
| 7,379,577 | B2 * | 5/2008 | King et al. | 382/133 |
| 7,564,623 | B2 * | 7/2009 | Vodyanoy et al. | 359/385 |
| 8,000,905 | B1 * | 8/2011 | Chen et al. | 702/35 |
| 2008/0037004 | A1 * | 2/2008 | Shamir et al. | 356/73 |
| 2010/0188499 | A1 * | 7/2010 | Amanullah et al. | 348/87 |
| 2012/0068068 | A1 * | 3/2012 | Hill et al. | 250/307 |

* cited by examiner

*Primary Examiner* — Christopher S Kelley
*Assistant Examiner* — Zhihan Zhou (57) ABSTRACT

A method and a particle analyzer are provided for determining a particle size distribution of a liquid sample including particles of a lower size range, particles of an intermediate size range, and particles of an upper size range. A dark-field image frame is captured in which the particles of the lower size range and the particles of the intermediate size range are resolved, and a bright-field image frame is captured in which the particles of the intermediate size range and the particles of the upper size range are resolved. Absolute sizes of the particles of the intermediate size range and the particles of the upper size range are determined from the bright-field image frame. Calibrated sizes of the particles of the lower size range are determined from the dark-field image frame by using the particles of the intermediate size range as internal calibration standards.

20 Claims, 5 Drawing Sheets

METHOD AND PARTICLE ANALYZER FOR DETERMINING A BROAD PARTICLE SIZE DISTRIBUTION

CROSS-REFERENCE TO RELATED APPLICATIONS

This application is a continuation of and claims priority to U.S. patent application Ser. No. 13/097,285, filed Apr. 29, 2011, entitled "Method and Particle Analyzer for Determining a Broad Particle Size Distribution," the disclosure of which is incorporated herein by reference in its entirety.

TECHNICAL FIELD OF THE INVENTION

The present invention relates to methods and particle analyzers for determining particle size distributions of liquid samples. More particularly, the present invention relates to methods and particle analyzers for determining particle size distributions by using bright-field and/or dark-field imaging.

BACKGROUND OF THE INVENTION

The determination of particle size distributions of liquid samples is necessary in pharmaceutical, life-science, and environmental-science applications, among others. The liquid samples may include dispersed particles of sizes ranging from less than 0.1 µm to 1000 µm. Generally, different types of particle analyzer are used to determine the sizes of particles of different size ranges.

Bright-field imaging particle analyzers may be used to determine the sizes of particles larger than about 0.5 µm in a liquid sample. For example, micro-flow imaging (MFI) particle analyzers are described in U.S. Pat. No. 7,064,826 to Rabinski, et al., issued on Jun. 20, 2006, in U.S. Pat. No. 7,217,937 to King, issued on May 15, 2007, in U.S. Pat. No. 7,307,721 to King, issued on Dec. 11, 2007, in U.S. Pat. No. 7,379,577 to King, et al., issued on May 27, 2008, and in U.S. Pat. No. 7,605,919 to Oma, et al., issued on Oct. 20, 2009, which are incorporated herein by reference. Other examples of bright-field imaging particle analyzers are described in U.S. Pat. No. 6,061,130 to Plate, et al., issued on May 9, 2000, and in U.S. Pat. No. 6,522,781 to Norikane, et al., issued on Feb. 18, 2003, which are incorporated herein by reference. By using such particle analyzers, particles of an upper size range in a liquid sample can be individually analyzed and visualized.

On the other hand, a dark-field imaging particle analyzer may be used to determine the sizes of particles smaller than about 1 µm in a liquid sample. For example, nanoparticle tracking analysis (NTA) particle analyzers are described in U.S. Pat. No. 6,280,960 to Can, issued on Aug. 28, 2001, and in U.S. Pat. No. 7,399,600 to Can, issued on Jul. 15, 2008, which are incorporated herein by reference. By using such particle analyzers, particles of a lower size range in a liquid sample can be individually analyzed and visualized. However, as NTA requires the capture of several dark-field image frames, the rate of analysis is relatively low.

Although both bright-field and dark-field imaging particle analyzers are separately known, the use of different particle analyzers to determine the sizes of particles of an upper size range and particles of a lower size range in the same liquid sample is highly inconvenient. Furthermore, the sizes determined by the different particle analyzers often disagree where the upper and lower size ranges overlap.

An imaging flow cytometer combining bright-field and dark-field imaging is described in U.S. Pat. No. 7,634,125 to Ortyn, et al., issued on Dec. 15, 2009, which is incorporated herein by reference. This imaging flow cytometer may be used to determine the sizes of cells in a liquid sample. However, cells of only a narrow size range, typically, about 5 µm to 15 µm, can be individually analyzed and visualized.

A particle analyzer combining bright-field imaging and laser-diffraction analysis is described in U.S. Pat. No. 7,471,393 to Trainer, issued on Dec. 30, 2008, which is incorporated herein by reference. This particle analyzer may be used to determine the sizes of particles of an upper size range and particles of a lower size range in a liquid sample. However, the particles of the lower size range cannot be individually analyzed or visualized. Rather, the particles of the lower size range are analyzed as an array, on the basis of their laser diffraction pattern.

Particle analyzers combining single-particle light-extinction and light-scattering analysis are described in U.S. Pat. No. 5,835,211 to Wells, et al., issued on Nov. 10, 1998, and in U.S. Pat. No. 6,794,671 to Nicoli, et al., issued on Sep. 21, 2004, which are incorporated herein by reference. These particle analyzers may be used to determine the sizes of particles of an upper size range and particles of a lower size range in a liquid sample. However, the size determination relies on a calibration curve determined by using external calibration standards and is prone to calibration errors arising from differences between the optical properties of the particles and the calibration standards. Moreover, the particles cannot be individually visualized.

Therefore, a particle analyzer combining bright-field and dark-field imaging that allows particles of an upper size range and particles of a lower size range in a liquid sample to be individually analyzed and visualized is highly desirable. Such a particle analyzer should provide consistent sizes throughout the upper and lower size ranges to enable a broad particle size distribution of the liquid sample to be accurately determined.

SUMMARY OF THE INVENTION

Accordingly, the present invention relates to a method a particle size distribution of a liquid sample with a particle analyzer; the liquid sample including particles of a lower size range that are resolvable by dark-field imaging, particles of an intermediate size range that are resolvable by dark-field imaging and by bright-field imaging, and particles of an upper size range that are resolvable by bright-field imaging; the particle analyzer including a sample cell, a dark-field light source, a bright-field light source, an imaging system, and a processing system including an analysis module; the method comprising: a) holding the liquid sample in the sample cell; b) illuminating the liquid sample in the sample cell with the dark-field light source in a dark-field geometry to yield scattered light; c) collecting, focusing, and detecting the scattered light with the imaging system to capture a dark-field image frame in which the particles of the lower size range and the particles of the intermediate size range are resolved; d) analyzing the dark-field image frame with the analysis module to locate images of the particles of the lower size range and the particles of the intermediate size range; e) analyzing the images of the particles of the lower size range and the particles of the intermediate size range with the analysis module to determine relative sizes of the particles of the lower size range and the particles of the intermediate size range; f) illuminating the liquid sample in the sample cell with the bright-field light source in a bright-field geometry to yield transmitted light; g) collecting, focusing, and detecting the transmitted light with the imaging system to capture a bright-field image frame in which the particles of the intermediate size range and the particles of the upper size range are resolved; h) analyzing the bright-field image frame with the analysis module to locate images of the particles of the intermediate size range and the particles of the upper size range; i) analyzing the images of the particles of the intermediate size range and the particles of the upper size range with the analysis module to determine absolute sizes of the particles of the intermediate size range and the particles of the upper size range; j) comparing the dark-field image frame and the bright field image frame with the analysis module to identify corresponding images of the particles of the intermediate size range located in both the dark-field image frame and the bright-field image frame; k) comparing the relative sizes and the absolute sizes of the particles of the intermediate size range that were determined by analyzing the corresponding images with the analysis module to determine a calibration curve; l) applying the calibration curve to the relative sizes of the particles of the lower size range with the analysis module to determine calibrated sizes of the particles of the lower size range; and m) determining the particle size distribution of the liquid sample from the calibrated sizes of the particles of the lower size range, and the absolute sizes of the particles of the intermediate size range and the particles of the upper size range with the analysis module.

Another aspect of the present invention relates to a particle analyzer for determining a particle size distribution of a liquid sample; the liquid sample including particles of a lower size range that are resolvable by dark-field imaging, particles of an intermediate size range that are resolvable by dark-field imaging and by bright-field imaging, and particles of an upper size range that are resolvable by bright-field imaging; the particle analyzer comprising: a sample cell for holding the liquid sample; a dark-field light source for illuminating the liquid sample in the sample cell in a dark-field geometry to yield scattered light; a bright-field light source for illuminating the liquid sample in the sample cell in a bright-field geometry to yield transmitted light; an imaging system for collecting, focusing, and detecting the scattered light to capture a dark-field image frame in which the particles of the lower size range and the particles of the intermediate size range are resolved, and for collecting, focusing, and detecting the transmitted light to capture a bright-field image frame in which the particles of the intermediate size range and the particles of the upper size range are resolved; and a processing system including an analysis module for analyzing the dark-field image frame to locate images of the particles of the lower size range and the particles of the intermediate size range, for analyzing the images of the particles of the lower size range and the particles of the intermediate size range to determine relative sizes of the particles of the lower size range and the particles of the intermediate size range; for analyzing the bright-field image frame to locate images of the particles of the intermediate size range and the particles of the upper size range, for analyzing the images of the particles of the intermediate size range and the particles of the upper size range to determine absolute sizes of the particles of the intermediate size range and the particles of the upper size range, for comparing the dark-field image frame and the bright field image frame to identify corresponding images of the particles of the intermediate size range located in both the dark-field image frame and the bright-field image frame, for comparing the relative sizes and the absolute sizes of the particles of the intermediate size range that were determined by analyzing the corresponding images to determine a calibration curve, for applying the calibration curve to the relative sizes of the particles of the lower size range to determine calibrated sizes of the particles of the lower size range, and for determining the particle size distribution of the liquid sample from the calibrated sizes of the particles of the lower size range, and the absolute sizes of the particles of the intermediate size range and the particles of the upper size range.

BRIEF DESCRIPTION OF THE DRAWINGS

The present invention will be described in greater detail with reference to the accompanying drawings, which represent exemplary embodiments thereof, wherein.

DETAILED DESCRIPTION OF THE INVENTION

The present invention provides a method and a particle analyzer for determining a broad particle size distribution of a liquid sample by using a combination of bright-field and dark-field imaging.

Typically, the liquid sample comprises particles of a broad overall size range of about 0.05 µm to 500 µm, the particles being dispersed in the liquid sample. The liquid sample comprises particles of a lower size range, particles of an intermediate size range, and particles of an upper size range. The particles of the lower size range and the particles of the intermediate size range are resolvable by dark-field imaging, meaning that images of particles of the lower size range and the particles of the intermediate size range are discernible and distinguishable in a dark-field image frame. The particles of the intermediate size range and the particles of the upper size range are resolvable by bright-field imaging, meaning that images of particles of the intermediate size range and the particles of the upper size range are discernible and distinguishable in a bright-field image frame. Preferably, the lower size range is of about 0.05 µm to 0.5 µm, the intermediate size range is of about 0.5 µm to 1 µm, and the upper size range is of about 1 µm to 500 µm. Typically, the concentration of particles in the liquid sample is less than about 10 000 000 particles/mL.

Figure 1:
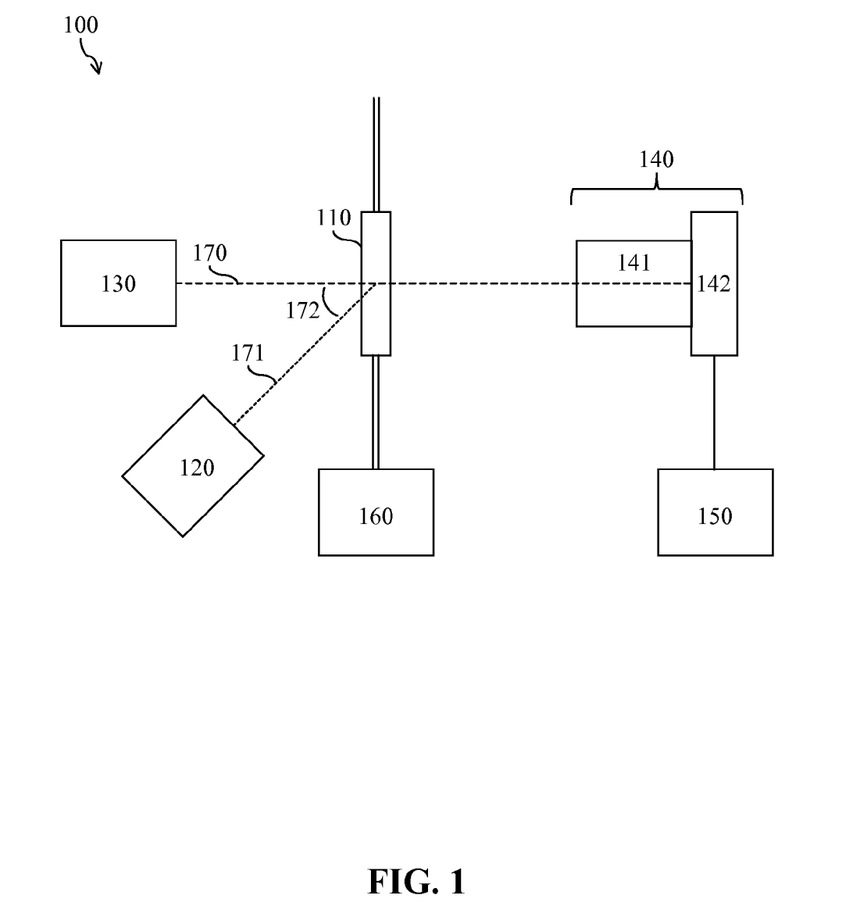
FIG. 1 is a schematic illustration of a first embodiment of a particle analyzer according to the present invention.

With reference to FIG. 1, a first embodiment of the particle analyzer 100 includes a sample cell 110, a dark-field light source 120, a bright-field light source 130, an imaging system 140, a processing system 150, and a pumping system 160. The imaging system 140 typically includes a magnification system 141 and a detector array 142. The processing system 150 typically includes a control module and an analysis module (not shown). The bright-field light source 130, the sample cell 110, the magnification system 141, and the detector array 142 are aligned along an optical axis 170. The dark-field light source 120 and the sample cell 110 are aligned along a direction 171 at an angle 172 to the optical axis 170.

Typically, the sample cell 110, which holds the liquid sample, is a flow cell. The pumping system 160 passes the liquid sample in a flowing stream into the sample cell 110. Preferably, the pumping system 160 is a pulse pumping system, as described in U.S. Pat. No. 7,307,721, which passes the liquid sample into the sample cell 110 with a pulse. Once the liquid sample is in the sample cell 110, the pumping system 160 substantially stops the stream to ensure that the liquid sample is substantially stationary in the sample cell 110 during image-frame capture. For example, the flow rate may be on the order of about 1 µm/s. After the liquid sample has been imaged, the pumping system 160, with another pulse, passes the liquid sample in the stream, now flowing once again, out of the sample cell 110, while passing a subsequent liquid sample in the stream into the sample cell 110.

The sample cell 110 is positioned to allow both the dark-field light source 120 and the bright-field light source 130 to illuminate the liquid sample, and is substantially transparent to light emitted from the dark-field light source 120 and the bright-field light source 130. The same optical sampling volume, which may be less than or equal to the volume of the sample cell 110, is illuminated by the dark-field light source 120 and the bright-field light source 130. The dark-field light source 120 and the bright-field light source 130 may be lamps, light-emitting diodes, lasers, or any other suitable light sources.

The dark-field light source 120 and the bright-field light source 130 may emit light in the same wavelength band or in different wavelength bands. For instance, when some of the particles in the liquid sample are fluorescent particles, which emit scattered fluorescent light in a first wavelength band after absorbing light in a second wavelength band, the dark-field light source 120 may be a fluorescent light source that illuminates the liquid sample in the sample cell 110 with light in the second wavelength band, and the bright-field light source 130 may illuminate the liquid sample in the sample cell 110 with light in the first wavelength band. A wavelength selective filter that passes only light in the first wavelength band to the detector array 142, while blocking light in the second wavelength band, may be included in the imaging system 140, as described in further detail hereafter.

The dark-field light source 120 illuminates the liquid sample in a dark-field geometry to yield scattered light. In other words, the dark-field light source 120 laterally illuminates the liquid sample to produce an image from light scattered by the liquid sample, in which particles appear bright against a dark background. The dark-field light source 120 illuminates the liquid sample along a direction 171 at an angle 172 to the optical axis 170 to ensure that a suitable scattered signal from the liquid sample is received by the imaging system 140, while minimizing unwanted scatter from the sample cell 110. The angle 172 may be any angle.

The bright-field light source 130 illuminates the liquid sample in a bright-field geometry to yield transmitted light. In other words, the bright-field light source 130 trans-illuminates the liquid sample to produce an image from light transmitted by the liquid sample, in which particles appear dark against a bright background. The bright-field light source 130 illuminates the liquid sample along the optical axis 170 to ensure that a suitable transmitted signal from the liquid sample is received by the imaging system 140.

The dark-field light source 120 and the bright-field light source 130 are separately activated, typically in alternation, so that either the scattered light yielded by the illumination of the liquid sample with the dark-field light source 120 or the transmitted light yielded by the illumination of the liquid sample with the bright-field light source 130 is received by the imaging system 140. Typically, the liquid sample is illuminated once with the dark-field light source 120 and once with the bright-field light source 130 to acquire a set of two image frames.

The magnification system 141 of the imaging system 140 collects the scattered light or the transmitted light and focuses it onto the detector array 142 of the imaging system 140. Typically, the magnification system 141 includes an objective, which may be an objective lens, a set of objective lenses of different magnifications, a variable-magnification lens system, or any other suitable objective, as well as one or more tube lenses. Preferably, the magnification system 141 also includes a diaphragm for enhancing diffraction enlargement, as described in U.S. Pat. No. 7,379,577.

The magnification system 141 of the imaging system 140 has a magnification factor and a numerical aperture selected to provide a suitable field of view and a suitable depth of field. The field of view of the magnification system 141, which corresponds to the cross-sectional area of the optical sampling volume, and the depth of field of the magnification system 141, which corresponds to the depth of the optical sampling volume, decrease as the magnification factor and the numerical aperture increase. The depth of field is usually small. For instance, the magnification system may have a magnification factor of 5, a field of view of about 2.2 mm$^2$, and a depth of field of about 100 µm, or a magnification factor of 10, a field of view of about 0.5 mm$^2$, and a depth of field of about 30 µm. Preferably, the liquid sample is confined to the maximum depth of field of the magnification system 141. For instance, the sample cell 110 may be designed to have a depth that is less than or equal to the maximum depth of field of the magnification system 141.

The detector array 142 of the imaging system 140 detects the scattered light or the transmitted light to capture a dark-field or bright-field image frame, respectively. The detector array 142 includes a plurality of detector elements. Typically, the detector array includes greater than 1 000 000 detector elements of about 4 µm to 6 µm in size. The detector array 142 detects the intensity of light incident on the plurality or detector elements and thereby captures a digital image frame formed of a plurality of pixels. The detector array 142 may be a charge-coupled device (CCD) array, a complementary metal-oxide semiconductor (CMOS) array, or any other suitable detector array.

Although it is preferred that a single detector array 142 of the imaging system 140 detects both the scattered light and the transmitted light, other embodiments may include two separate detector arrays 142 for detecting the scattered light and the transmitted light, respectively. For instance, in such an embodiment, the dark-field light source 120 and the bright-field light source 130 may emit light in two different wavelength bands, and two wavelength selective filters that each pass only light in one of the wavelength bands to a respective detector array 142, while blocking light in the other wavelength band, may be included in the imaging system 140.

A set of image frames, typically consisting of a dark-field image frame and a bright-field image frame, is captured for each liquid sample. In operation, the pumping system 160 passes the liquid sample in a flowing stream into the sample cell 110 and then substantially stops the stream. The dark-field light source 120 illuminates the liquid sample in the sample cell 110, and the detector array 142 of the imaging system 140 captures a dark-field image frame. The bright-field light source 130 illuminates the liquid sample in the sample cell 110, and the detector array 142 captures a bright-field image frame. The pumping system 160 then passes the liquid sample in the stream out of the sample cell 110, while passing a subsequent liquid sample in the stream, now flowing once again, into the sample cell 110. These steps are repeated until the required volume of liquid has been analyzed.

The time and intensity of illumination provided by the dark-field light source 120 and the bright-field light source 130 during image-frame capture, the flow rate of the liquid sample during image-frame capture as regulated by the pumping system 160, and the rate of image-frame capture by the detector array 142 of the imaging system 140 are selected to ensure that "freeze frame" conditions prevail as the set of image frames is captured, meaning that particles move by less than a significant fraction, typically about 5% to 15%, of their dimensions.

The control module of the processing system 150 controls the detector array 142 to determine the rate of image-frame capture. Preferably, the control module also controls the dark-field light source 120 and the bright-field light source 130 to determine the time of illumination, as well as the pumping system 160 to determine the flow rate. Thereby, the control module synchronizes the dark-field light source 120, the bright-field light source 130, the pumping system 160, and the detector array 142 of the imaging system 140 to ensure that the dark-field image frame and the bright-field image frame are successively captured, in either order, while the liquid sample is substantially stationary in the sample cell 110.

The processing system 150 receives the captured dark-field and bright-field image frames from the detector array 142 of the imaging system 140, stores the image frames, displays the image frames for viewing, and analyzes the image frames. Typically, the processing system 150 includes a memory and a suitably programmed processor, such as a central processing unit (CPU), a digital signal processor (DSP), a field-programmable gate array (FPGA), or any other suitable processor. The control module and the analysis module of the processing system 150 are typically implemented as software.

The analysis module of the processing system 150 records background intensities of each pixel when no sample particles are present in the sample cell 110. These background intensities are used to perform background subtraction and to minimize the effects of stuck particles or other fixed artifacts in the sample cell 110.

Figure 2:
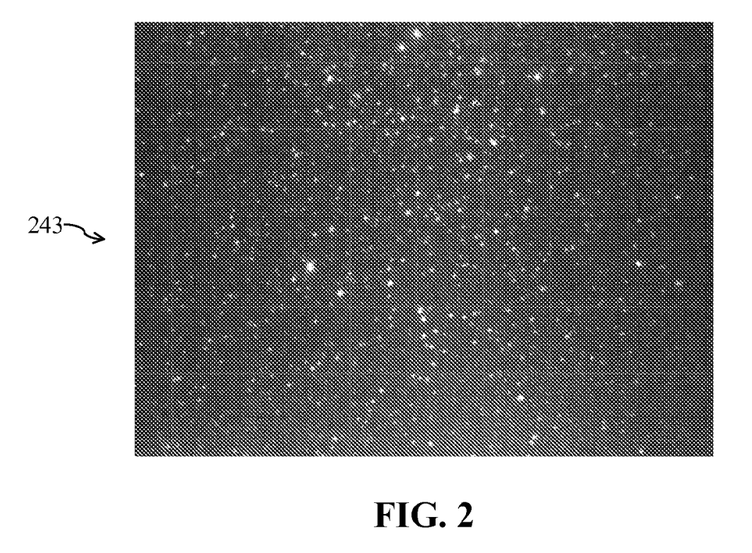
FIG. 2 is an exemplary dark-field image frame captured by a particle analyzer according to the present invention.

In the dark-field image frame, the particles of the lower size range and the particles of the intermediate size range are resolved. Generally, the particles of the upper size range are not resolved in the dark-field image frame because of blooming effects. Scattered particle images appear in the dark-field image frame as bright "stars" against a dark background. An exemplary dark-field image frame 243 is shown in FIG. 2.

The analysis module of the processing system 150 first analyzes the dark-field image frame to locate the images of the particles of the lower size range and the particles of the intermediate size range. The analysis module compares the intensity of each pixel in the digital image frame to a predetermined intensity threshold. The predetermined intensity threshold is selected to provide the most sensitive detection of pixels located wholly or partially in particle images, while minimizing incorrect counting of pixels whose intensity varies because of optical and/or electrical noise. If a cluster of adjacent pixels, typically at least 5 adjacent pixels, have intensities larger than the intensity threshold, the cluster is interpreted as a particle image, and the location of the particle image in the dark-field image frame is stored.

The analysis module of the processing system 150 then analyzes the located images of the particles of the lower size range and the particles of the intermediate size range by determining their sizes and intensities. The size of each particle image is determined by counting the pixels within the particle image. The intensity of each particle image is determined by averaging the intensities of the pixels within the particle image. The size and intensity of the particle image are dependent on the scattering power of that particle. The scattering power of the particle, in turn, is dependent on the size of the particle, as well as factors such as the optical properties of the particle, and the angles of illumination and detection. On this basis, the analysis module determines the relative sizes of the particles of the lower size range and the particles of the intermediate size range from the sizes and intensities of their particle images. However, as the scattering power of a particle increases rapidly with size, leading to oversaturation of the detector elements and blooming effects in the particle image, the relative sizes of the particles of the upper size range cannot be determined reliably.

Figure 3:
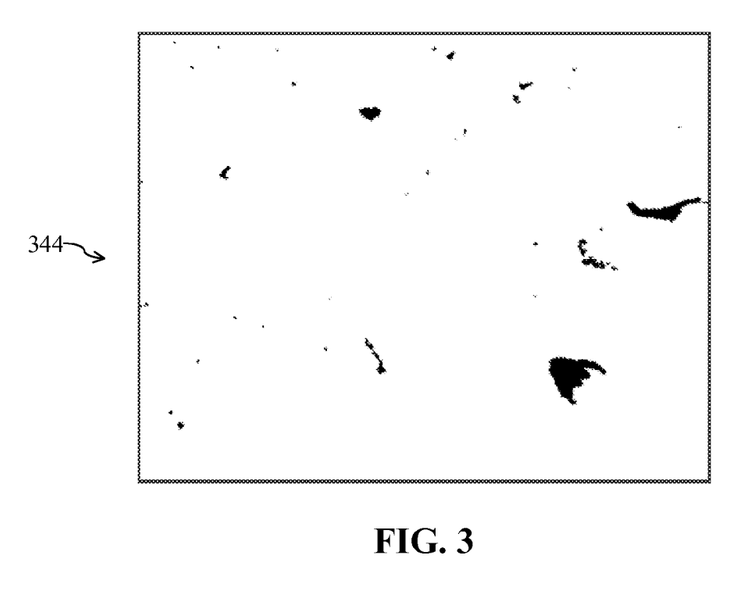
FIG. 3 is an exemplary bright-field image frame captured by a particle analyzer according to the present invention.

In the bright-field image frame, the particles of the intermediate size range and the particles of the upper size range are resolved. Generally, the particles of the lower size range are not resolved in the bright-field image frame because of insufficient contrast. Transmitted particle images appear in the bright-field image frame as dark shadows against a bright background. An exemplary bright-field image frame 344 is shown in FIG. 3.

The analysis module of the processing system 150 first analyzes the bright-field image frame to locate the images of the particles of the intermediate size range and the particles of the upper size range. The analysis module compares the intensity of each pixel in the digital image frame to a predetermined intensity threshold. The predetermined intensity threshold is selected to provide the most sensitive detection of pixels located wholly or partially in particle images, while minimizing incorrect counting of pixels whose intensity varies because of optical and/or electrical noise. If a cluster of adjacent pixels, typically at least 5 adjacent pixels, have intensities smaller than the intensity threshold, the cluster is interpreted as a particle image, and the location of the particle image in the bright-field image frame is stored.

The analysis module of the processing system 150 then analyzes the located images of the particles of the intermediate size range and the particles of the upper size range by determining their sizes. The size of each particle image is determined by counting the number of pixels within the particle image. The size of the particle image is related to the size of that particle by the magnification factor of the magnification system 141 and any additional diffraction enlargement. Advantageously, the size of the particle image is substantially independent of factors such as the optical properties of the particle. On this basis, the analysis module determines the absolute sizes of the particles of the intermediate size range and the particles of the upper size from the sizes of their particle images. However, as the interaction of a particle with the bright-field illumination decreases with size, leading to insufficient contrast between the particle image and the background, and to an insufficient number of pixels in the particle image, absolute sizes of the particles of the lower size range cannot be determined reliably. In some instances, it may be desirable to use contrast enhancement techniques, as described in U.S. Pat. No. 7,605,919.

The analysis module of the processing system 150 compares the dark-field image frame and the bright-field image frame to identify corresponding images of the particles of the intermediate size located in both the dark-field image frame and the bright-field image frame. For each particle image in the dark-field image frame, the analysis module compares its stored location with the stored locations of the particle images in the bright-field image frame. If the stored locations of a set of particle images differ by less than a predetermined displacement threshold, the set of particle images are interpreted as corresponding images of the same particle of the intermediate size range. For example, the predetermined displacement threshold may be less than about 5% of the length of the field of view and less than about 1% of the width of the field of view.

In effect, the particles of the intermediate size range, for which corresponding particle images are located in the dark-field and the bright-field image frames, serve as internal calibration standards. The analysis module of the processing system 150 determines a calibration curve by comparing the relative sizes and the absolute sizes of the particles of the intermediate size range, which were determined by analyzing the corresponding images of the particles of the intermediate size range located in the dark-field image frame and the bright-field image frame, respectively. Generally, the calibration curve is generated by fitting the size data, for example, by using a polynomial function. Typically, a look-up table is also generated.

The analysis module of the processing system 150 then applies the calibration curve to the relative sizes of the particles of the lower size range to determine calibrated sizes of the particles of the lower size range. In other words, the analysis module uses the calibration curve to convert the relative sizes of the particles of the lower size range, which were determined by analyzing the images of the particles of the lower size range located in the dark-field image frame, to calibrated sizes.

Finally, the analysis module of the processing system 150 determines the particle size distribution of the liquid sample from the calibrated sizes of the particles of the lower size range, and the absolute sizes of the particles of the intermediate size range and the particles of the upper size range. Typically, the analysis module of the processing system 150 also displays the particle size distribution for viewing.

Figure 4A:
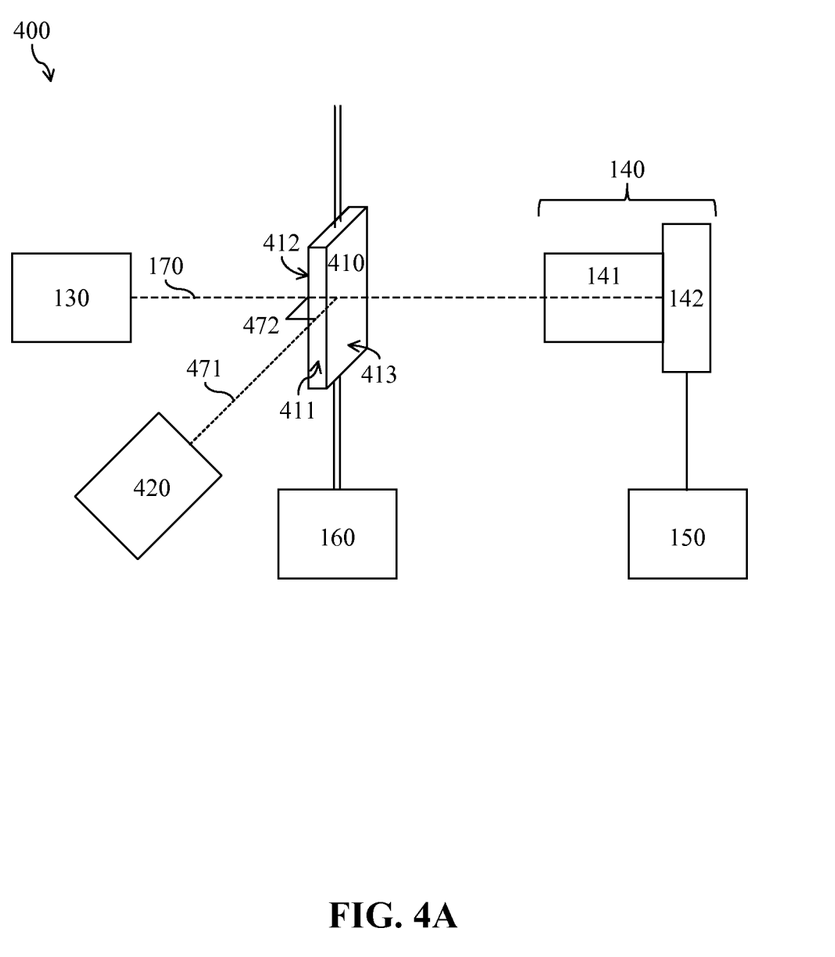
FIG. 4A is a schematic illustration of a second embodiment of a particle analyzer according to the present invention.
Figure 4B:
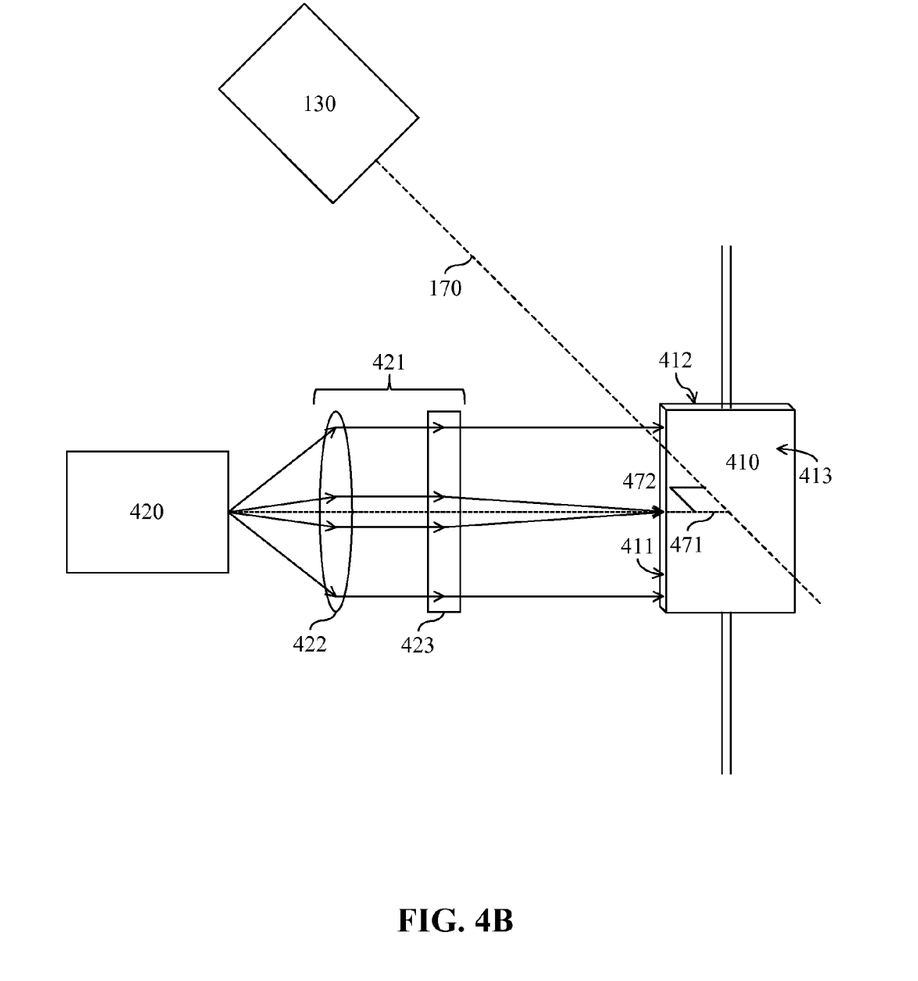
FIG. 4B is a schematic illustration of a dark-field light source, a bright-field light source, a sheet-forming system, and a sample cell of the particle analyzer of FIG. 4A.

With reference to FIGS. 4A and 4B, a second embodiment of the particle analyzer 400 is similar to the first embodiment, but includes a specially adapted sample cell 410, and a dark-field light source 420 that is aligned with the sample cell 410 along a direction 471 at an angle 472 of about 90° to the optical axis 170.

The specially adapted sample cell 410 includes a side window 411 that is substantially transparent to light emitted from the dark-field light source 420. The sample cell 410 also includes a front window 412 and a back window 413 that are substantially transparent to light emitted from the bright-field light source 130. Preferably, the front window 412 and the back window 413 are substantially parallel and are separated by a depth that is less than or equal to the maximum depth of field of the magnification system 141. For example, the sample cell 110 may have a depth of about 100 µm or about 30 µm.

The sample cell 410 is positioned such that the side window 411 receives light from the dark-field light source 420 and the front window 412 receives light from the bright-field light source 130. The dark-field light source 420 illuminates the liquid sample along the direction 471 substantially orthogonal to the optical axis 170, and as in the first embodiment, the bright-field light source 130 illuminates the liquid sample along the optical axis 170.

With particular reference to FIG. 4B, preferably, the dark-field light source 420 is a laser, and the particle analyzer 400 includes a sheet-forming system 421, which is positioned between the dark-field light source 420 and the sample cell 410. The sheet-forming system 421 forms the light emitted from the dark-field light source 420 into a light sheet substantially parallel to the front window 412 and the back window 413, and directed into the side window 411 of the sample cell 410.

In one embodiment, the sheet-forming system 421 includes a spherical lens 422 and a cylindrical lens 423. The spherical lens 422 collimates the light emitted from the dark-field light source 420, and the cylindrical lens 423 focuses the collimated light into a light sheet directed into the side window 411 of the sample cell 410. Any other suitable embodiment of a sheet-forming system may also be used.

Typically, the focused light sheet, in free space, has a Gaussian intensity distribution, and the intensity of the light sheet varies along its direction of propagation and along its narrow direction. These intensity variations can reduce the resolution with which particles of different sizes can be distinguished.

Advantageously, the sample cell 410 reduces such intensity variations in the light sheet by effectively serving as an optical waveguide. The front window 412 and the back window 413 of the sample cell 410 serve as highly reflective, substantially parallel walls, separated by a narrow depth. The high degree of reflection results from the low angle of incidence of the light sheet on the front window 412 and the back window 413. The reflection is further enhanced by ensuring that the polarization axis of the light sheet lies in a plane substantially parallel to the front window 412 and the back window 413. When propagating through the sample cell 410, the light sheet is partially confined and diverges to a lesser degree than it would in free space. The partial confinement also reduces the angular accuracy with which the light sheet must be directed between the front window 412 and the back window 413. Preferably, the front window 412 and the back window 413 are formed of a low-index glass, such as silica.

Figure 5:
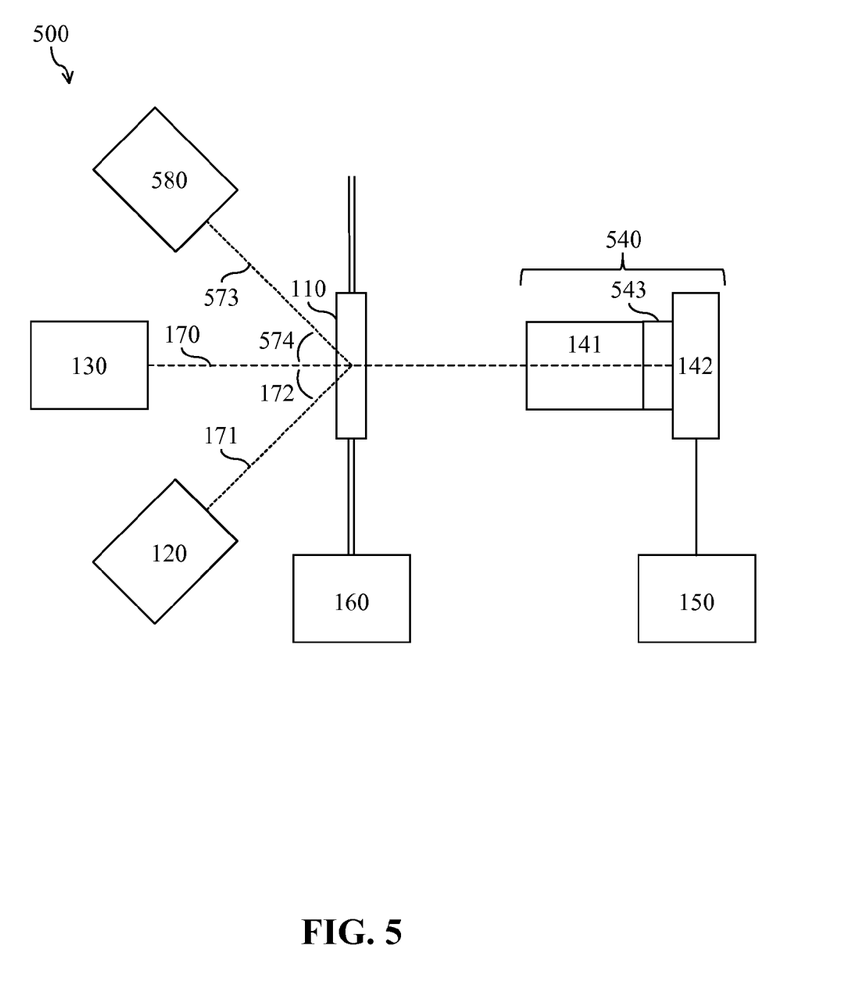
FIG. 5 is a schematic illustration of a third embodiment of a particle analyzer according to the present invention.

With reference to FIG. 5, a third embodiment of the particle analyzer 500 is useful in instances where some of the particles in the liquid sample are fluorescent particles, having either natural fluorophores or fluorophore tags, which emit fluorescent light in a first wavelength band after absorbing light in a second wavelength band.

The third embodiment of the particle analyzer 500 is similar to the first embodiment, but includes an additional fluorescence light source 580 that is aligned with the sample cell 110 along a direction 573 at an angle 574 to the optical axis 170, and an imaging system 540 comprising a wavelength selective filter 543. The angle 574 may be any angle.

The fluorescence light source 580 illuminates the liquid sample in the sample cell 110 with light in the second wavelength band to yield fluorescent light in the first wavelength band, as well as scattered light in the second wavelength band. The dark-field light source 120 and the bright-field light source 130 illuminate the liquid sample in the sample cell 110 with light in the first wavelength band to yield scattered light or transmitted light, respectively, in the first wavelength band. Typically, the liquid sample is illuminated once with the dark-field light source 120, once with the bright-field light source 130, and once with the fluorescence light source 580 to capture a set of three image frames, consisting of a dark-field image frame, a bright-field image frame, and a fluorescence image frame. The dark-field image frame, the bright-field image frame, and the fluorescence image frame are successively captured, in any order, while the liquid sample is substantially stationary in the sample cell 110, that is, under "freeze frame" conditions, as described heretofore.

The wavelength selective filter 543 of the imaging system 540 passes the scattered light, the transmitted light, and the fluorescent light in the first wavelength band to the detector array 142 of the imaging system 540, while blocking the scattered light in the second wavelength band. The wavelength selective filter 543 is preferably positioned within the magnification system 141 of the imaging system 540, but may also be positioned between the magnification system 141 and the detector array 142 or between the sample cell 110 and the magnification system 141.

Accordingly, the magnification system 141 of the imaging system 540 collects and focuses the scattered light, the transmitted light, or the fluorescent light in the first wavelength band onto the detector array 142 of the imaging system 540. The detector array 142 detects the scattered light, the transmitted light, or the fluorescent light in the first wavelength band to capture a dark-field, bright-field, or fluorescence image frame, respectively.

The processing system 150 receives the captured dark-field, bright-field, and fluorescence image frames from the detector array 142, stores the image frames, displays the image frames for viewing, and analyzes the image frames. The dark-field and bright-field image frames are analyzed as described heretofore.

The analysis module of the processing system 150 first analyzes the fluorescence image frame to locate images of the fluorescent particles. The analysis module compares the intensity of each pixel in the digital image frame to a predetermined intensity threshold. The predetermined intensity threshold is selected to provide the most sensitive detection of pixels located wholly or partially in particle images, while minimizing incorrect counting of pixels whose intensity varies because of optical and/or electrical noise. If a cluster of adjacent pixels, typically at least 5 adjacent pixels, have intensities larger than the intensity threshold, the cluster is interpreted as a particle image, and the location of the particle image in the fluorescence image frame is stored.

The analysis module of the processing system 150 then compares the dark-field, bright-field, and fluorescence image frames to identify corresponding images of the fluorescent particles in the fluorescence image frame and in either or both of the dark-field and bright-field image frames. For each particle image in the fluorescence image frame, the analysis module compares its stored location with the stored locations of the particle images in the dark-field and bright-field image frames. If the stored locations of a set of particle images differ by less than a predetermined displacement threshold, the set of particle images are interpreted as corresponding images of the same fluorescent particle. For example, the predetermined displacement threshold may be less than about 5% of the length of the field of view and less than about 1% of the width of the field of view.

Thereby, the analysis module of the processing system 150 may identify images of the fluorescent particles of the lower size range and the fluorescent particles of the intermediate size range in the dark-field image frame, and may identify images of the fluorescent particles of the intermediate size range and the fluorescent particles of the upper size range in the bright-field image frame. Furthermore, the analysis module may determine a size distribution of only the fluorescent particles in the liquid sample from the calibrated sizes of the fluorescent particles of the lower size range, and the absolute sizes of the fluorescent particles of the intermediate size range and the fluorescent particles of the upper size range.

Of course, numerous other embodiments may be envisaged without departing from the spirit and scope of the invention.

We claim:

1. A method comprising:
holding a liquid sample in the sample cell a particle analyzer, the liquid sample including (1) particles of a lower size range that are resolvable by dark-field imaging, (2) particles of an intermediate size range that are resolvable by dark-field imaging and by bright-field imaging, and (3) particles of an upper size range that are resolvable by bright-field imaging, the particle analyzer including the sample cell, a dark-field light source, a bright-field light source, an imaging system and a processing system;
illuminating the liquid sample in the sample cell with the dark-field light source in a dark-field geometry to produce a scattered light;
detecting the scattered light with the imaging system to capture a dark-field image frame in which the particles of the lower size range and the particles of the intermediate size range are resolved;
analyzing the dark-field image frame with the analysis module of the processing system to locate images of the particles of the lower size range and the particles of the intermediate size range;
analyzing the images of the particles of the lower size range and the particles of the intermediate size range from the dark-field image frame with the analysis module of the processing system to determine relative sizes of the particles of the lower size range and the particles of the intermediate size range;
illuminating the liquid sample in the sample cell with the bright-field light source in a bright-field geometry to produce a transmitted light;
detecting the transmitted light with the imaging system to capture a bright-field image frame in which the particles of the intermediate size range and the particles of the upper size range are resolved;
analyzing the bright-field image frame with the analysis module of the processing system to locate images of the particles of the intermediate size range and the particles of the upper size range;
analyzing the images of the particles of the intermediate size range and the particles of the upper size range from the bright-field image frame with the analysis module of the processing system to determine absolute sizes of the particles of the intermediate size range and the particles of the upper size range;
comparing the dark-field image frame and the bright field image frame with the processing system to identify corresponding images of the particles of the intermediate size range located in both the dark-field image frame and the bright-field image frame;
comparing the relative sizes and the absolute sizes of the particles of the intermediate size range that were determined by analyzing the corresponding images with the analysis module to determine a calibration curve;
applying the calibration curve to the relative sizes of the particles of the lower size range with the analysis module to determine calibrated sizes of the particles of the lower size range; and
determining the particle size distribution of the liquid sample from the calibrated sizes of the particles of the lower size range, and the absolute sizes of the particles of the intermediate size range and the particles of the upper size range with the processing system.

2. The method of claim 1, wherein the lower size range is of about 0.05 μm to 0.5 μm, the intermediate size range is of about 0.5 μm to 1 μm, and the upper size range is of about 1 μm to 500 μm.

3. The method of claim 1, wherein:
the imaging system includes a magnification system and a detector array;
detecting the scattered light to capture a dark-field image frame includes collecting and focusing the scattered light onto the detector array with the magnification system, and detecting the scattered light with the detector array to capture the dark-field image frame; and detecting the transmitted light to capture the bright-field image frame includes collecting and focusing the transmitted light onto the detector array with the magnification system, and detecting the transmitted light with the detector array to capture the bright-field image frame.

4. The method of claim 3, wherein the particle analyzer further includes a pumping system, the method further comprising:

passing the liquid sample in a flowing stream into the sample cell with the pumping system before holding the liquid sample in the sample cell; and substantially stopping the stream with the pumping system when the liquid sample is in the sample cell to ensure that the liquid sample is substantially stationary in the sample cell before detecting the scattered light to capture a dark-field image.

5. The method of claim 4, wherein the processing system further includes a control module, the method further comprising:

synchronizing the dark-field light source, the bright-field light source, the detector array, and the pumping system with the control module to ensure that the dark-field image frame and the bright-field image frame are successively captured while the liquid sample is substantially stationary in the sample cell.

6. The method of claim 3, wherein:

the bright-field light source, the sample cell, the magnification system, and the detector array are aligned along an optical axis;

the dark-field light source and the sample cell are aligned along a direction at an angle to the optical axis;

illuminating the liquid sample in the sample cell with the dark-field light source includes illuminating the liquid sample in the sample cell along the direction at an angle to the optical axis with the dark-field light source; and illuminating the liquid sample in the sample cell with the bright-field slight source includes illuminating the liquid sample in the sample cell along the optical axis with the bright-field light source.

7. The method of claim 6, wherein:

the dark-field light source and the sample cell are aligned along a direction at an angle of about 90 degrees to the optical axis; and illuminating the liquid sample in the sample cell with the dark-field light source includes illuminating the liquid sample in the sample along the direction at an angle of about 90 degrees to the optical axis.

8. The method of claim 7, wherein:

the particle analyzer further includes a sheet-forming system;

the sample cell includes a side window configured to receive light emitted from the dark-field light source, a front window configured to receive light emitted from the bright-field light source, and a back window substantially parallel to the front window and separated therefrom by a depth that is less than or equal to a maximum depth of field of the magnification system;

the dark-field light source is a laser; and illuminating the liquid sample in the sample cell with the dark-field light source further includes forming the light emitted from the dark-field light source into a light sheet substantially parallel to the front window and the back window of the sample cell, and directed into the side window of the sample cell with the sheet-forming system.

9. The method of claim 3, wherein:

at least some of the particles in the liquid sample are fluorescent particles that emit light in a first wavelength band after absorbing light in a second wavelength band;

the particle analyzer further includes a fluorescence light source;

the imaging system further includes a wavelength selective filter;

illuminating the liquid sample in the sample cell with the dark-field light source includes illuminating the liquid sample in the sample cell with light in the first wavelength band with the dark-field light source to yield scattered light in the first wavelength band;

detecting the scattered light to capture the dark-field image includes collecting and focusing the scattered light in the first wavelength band onto the detector array with the magnification system, and detecting the scattered light in the first wavelength band with the detector array to capture the dark-field image frame;

illuminating the liquid sample with the bright-field source includes illuminating the liquid sample in the sample cell with light in the first wavelength band with the bright-field light source to yield transmitted light in the first wavelength band; and detecting the transmitted light to capture a bright-field image frame includes collecting and focusing the transmitted light in the first wavelength band onto the detector array with the magnification system, and detecting the transmitted light in the first wavelength band with the detector array to capture the bright-field image frame;

the method further comprising:

illuminating the liquid sample in the sample cell with light in the second wavelength band with the fluorescence light source to yield fluorescent light in the first wavelength band and scattered light in the second wavelength band;

passing the scattered light, the transmitted light, and the fluorescent light in the first wavelength band to the detector array with the wavelength selective filter, while blocking the scattered light in the second wavelength band with the wavelength selective filter;

collecting and focusing the fluorescent light in the first wavelength band onto the detector array with the magnification system;

detecting the fluorescent light in the first wavelength band with the detector array to capture a fluorescence image frame;

analyzing the fluorescence image frame with the analysis module to locate images of the fluorescent particles; and comparing the fluorescence image frame, the dark-field image frame, and the bright-field image frame with the analysis module to identify corresponding images of the fluorescent particles located in the fluorescence image frame and in either or both of the dark-field image frame and the bright-field image frame.

10. An apparatus, comprising:

a particle analyzer configured to determine a particle size distribution of a liquid sample, the liquid sample including particles of a lower size range that are resolvable by dark-field imaging, particles of an intermediate size range that are resolvable by dark-field imaging and by bright-field imaging, and particles of an upper size range that are resolvable by bright-field imaging, the particle analyzer including:

a sample cell configured to hold the liquid sample;

a dark-field light source configured to illuminate the liquid sample in the sample cell in a dark-field geometry to produce scattered light;

a bright-field light source configured to illuminate the liquid sample in the sample cell in a bright-field geometry to produce transmitted light;

an imaging system configured to detect the scattered light to capture a dark-field image frame in which the particles of the lower size range and the particles of the intermediate size range are resolved, the imaging system configured to detect the transmitted light to capture a bright-field image frame in which the particles of the intermediate size range and the particles of the upper size range are resolved; and a processing system including an analysis module configured to:

analyze the dark-field image frame to locate images of the particles of the lower size range and the particles of the intermediate size range, determine relative sizes of the particles of the lower size range and the particles of the intermediate size range based on the dark-field image frame, analyze the bright-field image frame to locate images of the particles of the intermediate size range and the particles of the upper size range, determine absolute sizes of the particles of the intermediate size range and the particles of the upper size range based on the bright-field image frame, compare the dark-field image frame and the bright-field image frame to identify corresponding images of the particles of the intermediate size range located in both the dark-field image frame and the bright-field image frame, compare the relative sizes and the absolute sizes of the particles of the intermediate size range that were determined by analyzing the corresponding images to determine a calibration curve, apply the calibration curve to the relative sizes of the particles of the lower size range to determine calibrated sizes of the particles of the lower size range, and determine the particle size distribution of the liquid sample from the calibrated sizes of the particles of the lower size range, and the absolute sizes of the particles of the intermediate size range and the particles of the upper size range.

11. The particle analyzer of claim 10, wherein the lower size range is of about 0.05 μm to 0.5 μm, the intermediate size range is of about 0.5 μm to 1 μm, and the upper size range is of about 1 μm to 500 μm.

12. The particle analyzer of claim 10, wherein the imaging system includes:

a detector array configured to:

detect the scattered light to capture the dark-field image frame, and detect the transmitted light to capture the bright-field image frame; and a magnification system configured to:

collect and focus the scattered light onto the detector array, and collect and focus the transmitted light onto the detector array.

13. The particle analyzer of claim 12, wherein:

the detector array includes a charge-coupled device (CCD) array; and the magnification system includes an objective, one or more tube lenses, and a diaphragm.

14. The particle analyzer of claim 12, further comprising:

a pumping system configured to (1) pass the liquid sample in a flowing stream into the sample cell, and (2) substantially stop the stream when the liquid sample is in the sample cell to ensure that the liquid sample is substantially stationary in the sample cell.

15. The particle analyzer of claim 14, wherein the processing system further includes a control module configured to synchronize the dark-field light source, the bright-field light source, the detector array, and the pumping system to ensure that the dark-field image frame and the bright-field image frame are successively captured while the liquid sample is substantially stationary in the sample cell.

16. The particle analyzer of claim 12, wherein:

the bright-field light source, the sample cell, the magnification system, and the detector array are aligned along an optical axis;

the dark-field light source and the sample cell are aligned along a direction at a non-zero angle to the optical axis;

the dark-field light source is configured to illuminate the liquid sample in the sample cell along the direction at the non-zero angle to the optical axis; and the bright-field light source is configured to illuminate the liquid sample in the sample cell along the optical axis.

17. The particle analyzer of claim 16, wherein the non-zero angle is an angle of about 90 degrees.

18. The particle analyzer of claim 17, wherein the sample cell includes a side window configured to receive light emitted from the dark-field light source, a front window configured to receive light emitted from the bright-field light source, and a back window substantially parallel to the front window and separated therefrom by a depth that is less than or equal to a maximum depth of field of the magnification system.

19. The particle analyzer of claim 18, wherein the light source is a laser, the particle analyzer further comprising:

a sheet-forming system configured to form the light emitted from the dark-field light source into a light sheet substantially parallel to the front window and the back window of the sample cell, the sheet-forming system configured to direct the light sheet into the side window of the sample cell.

20. The particle analyzer of claim 12, wherein some of the particles in the liquid sample are fluorescent particles that emit light in a first wavelength band after absorbing light in a second wavelength band, the particle analyzer further comprising:

a fluorescence light source for illuminating the liquid sample in the sample cell with light in the second wavelength band to yield fluorescent light in the first wavelength band and scattered light in the second wavelength band, the dark-field light source is configured to illuminate the liquid sample in the sample cell with light in the first wavelength band to yield scattered light in the first wavelength band;

the bright-field light source is configured to illuminate the liquid sample in the sample cell with light in the first wavelength band to yield transmitted light in the first wavelength band;

the imaging system includes a wavelength selective filter for passing the scattered light, the transmitted light, and the fluorescent light in the first wavelength band to the detector array, while blocking the scattered light in the second wavelength band;

the magnification system is configured to:

collect and focus the scattered light in the first wavelength band onto the detector array, for collecting and focusing the transmitted light in the first wavelength band onto the detector array, and collect and focus the fluorescent light in the first wavelength band onto the detector array;

the detector array is configured to:

detect the scattered light in the first wavelength band to capture the dark-field image frame, detect the transmitted light in the first wavelength band to capture the bright-field image frame, and detect the fluorescent light in the first wavelength band to capture a fluorescence image frame; and the analysis module is configured to:

analyze the fluorescence image frame to locate images of the fluorescent particles, and compare the fluorescence image frame, the dark-field image frame, and the bright-field image frame to identify corresponding images of the fluorescent particles located in the fluorescence image frame and in at least one of the dark-field image frame or the bright-field image frame.

* * * * *